(12) United States Patent
Cedergren

(10) Patent No.: US 6,361,670 B1
(45) Date of Patent: Mar. 26, 2002

(54) DEVICE FOR COULOMETRIC DETERMINATION OF WATER BY THE KARL FISCHER METHOD

(75) Inventor: Anders Cedergren, Umeå(SE)

(73) Assignee: AB Stockholms Patentyra (SE)

( * ) Notice: Subject to any disclaimer, the term of this patent is extended or adjusted under 35 U.S.C. 154(b) by 0 days.

(21) Appl. No.: 09/331,828

(22) PCT Filed: Dec. 22, 1997

(86) PCT No.: PCT/SE97/02201

§ 371 Date: Aug. 27, 1999

§ 102(e) Date: Aug. 27, 1999

(87) PCT Pub. No.: WO98/28616

PCT Pub. Date: Jul. 2, 1998

(30) Foreign Application Priority Data

Dec. 23, 1996 (SE) .............................................. 9604771

(51) Int. Cl.$^7$ .............................................. G01N 27/44
(52) U.S. Cl. ..................... 204/405; 205/788; 205/788.5
(58) Field of Search ......................... 204/405; 205/788, 205/788.5

(56) References Cited

U.S. PATENT DOCUMENTS

| 2,928,782 A | * | 3/1960 | Leisey .................... 204/405 |
| 3,136,708 A | | 6/1964 | Czuha, Jr. et al. ............ 204/1 |
| 4,111,776 A | | 9/1978 | Mansfield .................. 204/195 |
| 4,133,733 A | * | 1/1979 | Moore ..................... 204/405 |
| 4,911,794 A | * | 3/1990 | Parce et al. ............... 204/415 |
| 5,139,955 A | | 8/1992 | Scholz ..................... 436/42 |
| 5,300,207 A | | 4/1994 | Dahms .................... 204/405 |

FOREIGN PATENT DOCUMENTS

| EP | 0 390 727 B1 | 1/1990 |
| WO | WO 95/13534 | 5/1995 |

* cited by examiner

*Primary Examiner*—T. Tung
(74) *Attorney, Agent, or Firm*—Brinks Hofer Gilson & Lione

(57) ABSTRACT

A device for the coulometric determination of water by a Karl Fischer reaction comprising a membrane-free measuring cell that contains a liquid reagent, an iodine indicating means, an anode, a cathode and a casing around the cathode to define a cathode space. The casing has an opening through which the cathode space communicates with the liquid reagent. A maneuverable drainage device including a plunger is provided to drain-off liquid reagent in the cathode space through the opening.

21 Claims, 1 Drawing Sheet

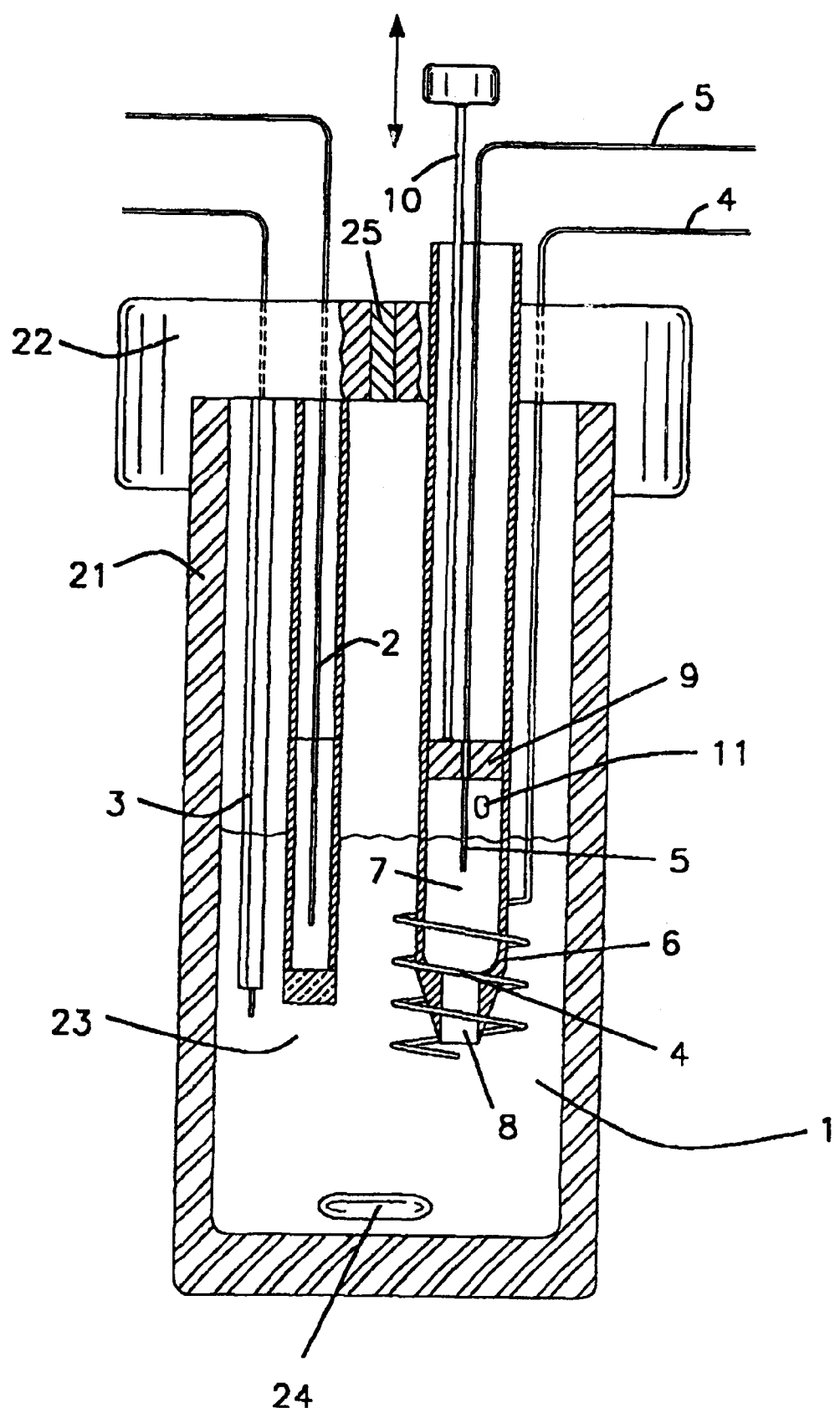

DEVICE FOR COULOMETRIC DETERMINATION OF WATER BY THE KARL FISCHER METHOD

The present invention relates to a method and to a device for coulometric determination of water by means of the Karl Fischer reaction in a membrane-free cell.

It is desirable in many cases to be able to determine the amount of water in a gas, a liquid, or in a solid material. This is normal, for instance, in the pharmaceutical industry, the lubricating oil industry, the foodstuff industry, etc. It is also desirable from several aspects to be able to determine the water concentration with the least possible chemical consumption.

The Karl Fischer reaction is well known to the person skilled in this art and, briefly, involves the consumption of water in a reaction with a Karl Fischer reagent that includes, among other things, iodine, sulphur dioxide and a base in a water-free solvent. The amount of water present can be determined, by measuring how much iodine is consumed.

By Karl Fischer reagent is meant here all reagents that satisfy the properties required by the Karl Fischer reaction. Such liquid reagents are well known to the person skilled in this art and will not therefore be described in detail here.

A well known problem with coulometric titration where one and the same Karl Fischer liquid reagent is in connection with both anode and cathode reside in interferences that result from the diffusion/migration of oxidizable reduction products generated in tee cathode reaction into the anode space where they react with the iodine that is generated at the anode and that is intended to react with the water present in the sample. The reduction products cam thus be said to simulate water, wherewith the analysis result becomes too high.

One solution to this problem is to adapt and use in the cathode space a special liquid which will not generate the interfering reduction products. In order to enable two separate liquids to be used in the cell, a membrane is placed between the liquids. In addition to practical handling problems, another drawback with membrane cells is that the membrane is very likely to become clogged, for instance when titrating oils, resulting in current limitations and therewith undesirably long titration times.

In accordance with known titration technology relatively high current pulses, e.g. from 400 mA, must be used when working with present day membrane-free cells. This is because reduction products are not generated to the same high extent at high currents. High currents, however, limit the choice of usable reaction mixtures, meaning that not all types of samples can be analyzed. No solution has yet been proposed in this line of development with respect to the actual problem of handling the reduction products. Instead, the development of membrane-free cells has been concentrated on finding combinations of high currents (for rapid titration) and reagents which generate low concentrations of reduction products at current levels in question.

An example in this regard is found in U.S. Pat. No. 5,300,207 which teaches a high current coulometric titrator for the Karl Fischer determination of water in a membrane-free cell. The iodine generating electrodes are configured such that the cathode has a small extension and the anode has a cupped shape which is open to the cathode, wherein the distance travelled by the electric current is the same from all points on the anode surface to the cathode. This is intended to improve iodine production. Also described is the arrangement of a tube over the cathode for channelling gas generated at the cathode up to the surface of the liquid so as to prevent the gas from interfering with the liquid flow. The tube is described as having holes which ensure circulation of the liquid reagent around the cathode.

An object of the present invention is to overcome the aforesaid drawbacks and to provide a device and a method for the determination of water in a membrane-free cell by means of the Karl Fischer reaction where the user has control over the oxidation of titration-interfering reduction products and is able to regulate such oxidation. Another object of the invention is to provide a device with which titration can be performed even at low currents and with all types of Karl Fischer reagents.

This object is achieved with a device and a method of the kind defined above that have the characteristic set forth in the claims.

It has surprisingly been found that the reliability of the titration results obtained is substantially improved when that part of the liquid reagent located nearest the cathode is prevented from circulating around in the cell together with the remaining liquid reagent.

Because the liquid present around the cathode is stationary, reduction products formed merely represent a local increase in the concentration of said products. They do not then influence the initial titration result. Between two titrations, when the concentration has reached a level at which the risk of migration increases, the cathode liquid can then be mixed with the remaining liquid reagent, wherewith the reduction products are oxidized normally in the course of titration.

The inventive device for coulometric determination of water by means of the Karl Fischer reaction includes a membrane-free measuring cell containing a Karl Fischer type liquid reagent, a means for measuring the level of iodine in the reagent and regulating titration current, and an anode and a cathodic which are spaced from one another and extend down into the liquid reagent, wherein the cathode electrode is disposed in a casing that screens-off in the measuring cell a cathode space between the inner surface of said casing and the cathode, and wherein the casing includes an opening through which the cathode space communicates with the measuring cell liquid reagent that penetrates to a level in the cathode space, and wherein there is arranged in the proximity of the casing a drainage means which when activated causes cathode liquid to flow out through said opening.

The casing may be a tubular element of generally constant internal cross-section and extending down into the liquid reagent with the opening at its free end. The drainage means may be a tillable chamber, an actuatable propeller, or a plunger.

The plunger may have a profile that is complementary to the inner profile of the casing, so as to essentially lie in abutment with the inner surface of the casing The plunger may also be comprised of a shape-pliable material, so that the plunger will be able to seat against the inner walls of the casing irrespective of minor variations in profile.

The cathode may be an electrically conductive wire that had been coated with an electrically non-conductive material and from which the non-conductive material has been removed over a determined surface area of the wire located beneath the liquid surface, so that a constant and small cathode area will be in conductive contact with the liquid reagent, this area being independent of changes in the level of reagent.

The anode may be disposed around the casing. In one embodiment, the anode has the form of a wire wound helically around the casing. In alternative embodiments, the anode may be a braided structure or a net-like structure, e.g. a basin or basket-like structure.

The cathode may be fixedly mounted on the plunger Alternatively, the plunger may be displaceable in relation to the cathode, wherewith in one embodiment the plunger includes a hole through which the cathode wire extends into the cathode space when the plunger is in its retracted position.

The casing wall has provided therein a hole which is located at a distance above the surface of the liquid reagent and downwardly of the plunger when said plunger is in its retracted position, wherewith the liquid level in the cathode space adopts the same level as the surrounding liquid by virtue of pressure equalization, therewith eliminating the risk that hydrogen gas generated by the cathode reaction will fill the cathode space and displace The liquid.

The casing opening located beneath the surface of the liquid will preferably be narrower than the internal cross-sectional area of the casing, therewith further amplifying the screening effect.

The inventive method of coulometrically determining water with a Karl Fischer reaction in a membrane-free cell that includes a liquid reagent, an anode and a cathode and wherein an open cathode space is disposed around the cathode comprises the steps of forcing from the cathode space liquid reagent which contains oxidizable reduction products that have been generated in the cathode reaction and mixing said liquid reagent with remaining liquid reagent, allowing the reduction products to react with iodine in the liquid reagent, again supplying a part of the liquid reagent to the cathode space, and delivering a sample to the liquid reagent located outside the cathode space while taking titration readings in a manner known per se.

Further features of the invention and advantages afforded thereby will be apparent from the following detailed description of a preferred embodiment of the invention, this embodiment being described by way of example only and is not therefore limitive to the scope of the present invention. The various components of the illustrated device have been designated reference numerals to facilitate an understanding of the description.

BRIEF DESCRIPTION OF THE DRAWINGS

FIG. 1 is a schematic, partly broken illustration of a device for coulometrically determining water by means of the Karl Fischer method, in a membrane-free cell according to one embodiment of the present invention.

Shown in FIG. 1 is a cylindrical vessel 21 with a tightly sealing cap or lid 22. The cap may be screwed onto the vessel, or secured thereto in some other suitable manner, e.g. with the aid of clamps, said vessel ideally being comprised of a transparent material. A packing may be disposed between the vessel and the cap, to minimize migration of moisture into the vessel from the surroundings.

The vessel contains a liquid reagent 23 of the Karl Fischer type, and a stirrer 24. The stirrer functions to circulate liquid reagent past the anode. In the illustrated case, the stirrer is a magnetic rod that is driven in a known manner. As will be evident from FIG. 1, the reagent may be included to a level slightly above half the height of the vessel, therewith leaving an air volume above the surface of the liquid. In one particularly preferred embodiment, the vessel is filled within a range of 70–80%.

A titration device extends through the cap and down into the liquid reagent. In the illustrated case, the titration device includes a reference means 2 and an indicator 3 which measures and registers the concentration of iodine in the reagent, and an anode 4 and a cathode 5 which generate iodine when current migrates therebetween.

With the intention of restricting the spread of those reduction products that are generated at the cathode, the cathode 5 is encased in a casing 6. The casing screens-off that part of the liquid reagent that is located nearest the cathode, by defining a cathode space 7. The liquid contained in the cathode space 7 will essentially stand still around the cathode, whereas the remainder of the liquid reagent circulates and is mixed/stirred by the stirrer. Since the casing is open beneath the level of the liquid reagent, current is able to migrate between anode and cathode.

Although there are no actual restrictions with regard to the size and shape of the vessel, the vessel may have a volumetric capacity of from 10–50 $cm^3$ in the case of analyzing smaller samples, and the liquid volume delimited by the casing may be in the range of 0.25–5 $cm^2$, preferably 0.25–1 $cm^3$.

The vessel 21 or the cap 22 may include an appropriate inlet through which the samples to be titrated can be delivered to the vessel. This inlet may, e.g., have the form of an autoinjector, a conduit, a hose or a material 25, such as rubber, that can be penetrated repeatedly by an injection needle.

The device includes an externally maneuverable plunger 9 mounted inside the casing 6. As will be evident from FIG. 1, the plunger 9 is connected slightly above the surface of the liquid to a rod 10 that extends inside the casing and projects out of the vessel. Ideally, a seal (not shown) is provided between the rod and the casing, with the intention of restricting the ingress of moisture from the surroundings. The user is able to push the plunger 9 towards the opening 8 when considered suitable, so as to expel, drain, the liquid reagent that is screened-off in the cathode space 7. The level of liquid reagent in the cathode space 7 is reestablished, by retracting the plunger.

In a vessel containing 40 $cm^3$ liquid reagent, a tubular casing is disposed over a cathode such as to screen-off a cathodic liquid volume of about 1 $cm^3$. The cathode is a platinum wire, 0.5 mm diameter, coated with a nonconductive polymer layer. The polymer layer is removed at the free end of the wire, over a surface area in the range of 0.01 to 0.1 $cm^2$. The anode is a platinum wire, 0.5 mm in diameter, wound helically around the casing to a level beneath the opening in said casing.

The reaction the generates the iodine necessary for the analysis at the anode also results in a reduction at the cathode of reduction products other than inert hydrogen gas, particularly at low currents. These successively increase in concentration in the cathode space 7 and subsequent to having analyzed a couple of samples, the reduction product concentration may be so high as to cause said products to begin to leave the cathode space. The user will suitably drain off the cathode liquid with the aid of the plunger between two samples analyses before this occurs, wherewith the reduction products can be allowed to oxidize while consuming iodine without interfering with an analysis.

One method of identifying the time at which this drainage should be effected is to monitor the development of the background current at the end of a titration process. An increase in the background current of 10 to 20% is normally an indication that it is time to drain-off the cathode liquid. This knowledge also enables draining of the cathode space to be automated, when the control system is permitted to maneuver the plunger. In this case, the plunger can be connected to a cathode space emptying device that can be actuated by electric signals. For instance, the plunger, or the plunger rod, can be actuated by an electric motor, or an electrically operatable valve can be connected to a pneumatically operatable piston-cylinder device connected to the plunger.

The analysis is further improved by continuously regulating the titration current instead of discrete regulation with a pulsed current. This is made possible by an indicator electrode system based on so-called zero current potentiometry.

The indicator electrode is an insulated platinum wire, diameter 0.5 mm. The solution for insulation is removed from the free end of the wire that projects into the liquid, through a distance of 0.5 cm.

The vessel has arranged therein a reference electrode which includes a platinum wire held in a glass tube whose free end is provided with a Vycor-glass plug crimped firmly on said end. The reference electrode is filled with a spent Karl Fischer solution comprising 0.20 M iodide, 5 M imidazole, 0.5 M sulphur dioxide to which 1 $\mu$l water is added for each 5 ml solution.

The transparent material from which the vessel is made may be glass or a transparent plastic material, although polymethyl pentene is preferred. Polymethyl pentene has the advantage that water will not bind to its surface as firmly as it binds to a glass surface. Although this may seem to have only a slight significance, it nevertheless, has a significant influence on the suitability of the vessel in the application concerned here.

What is claimed is:

1. A device for the coulometric determination of water by means of a Karl Fischer reaction, comprising a membrane-free measuring cell (1) that contains a Karl Fischer liquid reagent, an iodine indicating means (2,3), and an anode (4) and a cathode (5) that are spaced mutually apart and extend down into the liquid reagent, characterized in that the device further includes a casing (6) which is disposed around the cathode (5) to screen-off in the measuring cell (1) a cathode space (7) between the inner surface of the casing and the cathode; in that the casing (6) includes an opening (8) through which the cathode space (7) is placed in communication with measuring-cell liquid reagent that penetrates to a level in the cathode space; and in that a maneuverable drainage device (9, 10), including a plunger, is provided in the proximity of the casing and functions to drain-off cathode space liquid reagent through said opening when said plunger is actuated in this sense.

2. A device according to claim 1, characterized in that the casing (6) is a tubular element of essentially constant internal cross-sectional area and extends down into the liquid reagent with the opening (8) at a free end of said tubular element; in that the plunger (9) has a profile complementary to an inner profile of the casing; and in that the plunger (9) is movably mounted inside the casing (6), such that displacement of the plunger (9) towards said opening (8) will drive liquid reagent from the cathode space (7) and retraction of the plunger will reestablish a liquid reagent level in the cathode space (7).

3. A device according to claim 1 or 2, characterized in that the cathode (5) is an electrically conducted wire coated with an electrically non-conductive material; and in that the non-conductive material has been removed from a given surface area of the wire disposed beneath the surface of said liquid, wherewith a constant cathode surface area will be in conductive contact with the liquid reagent irrespective of changes in the level of liquid reagent.

4. A device according to claim 3, characterized in that the cathode (5) is fixedly mounted to the plunger (9).

5. A device according to claim 3, characterized in that the plunger (9) is displaceable in relation to the anode (4).

6. A device according to claim 5, characterized in that the plunger (9) has a hole formed therein through which the cathode (5) projects into the cathode space (7) when the plunger (9) is in its retracted position.

7. A device according to claim 3, characterized in that the casing (6) includes a through-penetrating hole that is spaced above the surface of liquid reagent and below the plunger when said plunger is in its retracted position, wherewith the level of liquid in the cathode space (7) adopts the same level as the surrounding liquid by virtue of pressure equalization; and in that the opening (8) has a narrower cross-sectional area than the internal cross-sectional area of said casing.

8. A device according to claim 1 or 2, characterized in that the anode (4) is disposed around the casing (6).

9. A device according to claim 8, characterized in that the anode (4) is a wire that is wound helically around the casing (6).

10. A device according to claim 9, characterized in that the cathode (5) is fixedly mounted to the plunger (9).

11. A device according to claim 9, characterized in that the plunger (9) is displaceable in relation to the cathode (5).

12. A device according to claim 11, characterized in that the plunger (9) has a hole formed therein through which the cathode (5) projects into the cathode space (7) when the plunger (9) is in its retracted position.

13. A device according to claim 9, characterized in that the casing (6) includes a through-penetrating hole that is spaced above the surface of liquid reagent and below the plunger when said plunger is in its retracted position, wherewith the level of liquid in the cathode space (7) adopts the same level as the surrounding liquid by virtue of pressure equalization; and in that the opening (8) has a narrower cross-sectional area than the internal cross-sectional area of said casing.

14. A device according to claim 8, characterized in that the cathode (5) is fixedly mounted to the plunger (9).

15. A device according to claim 8, characterized in that the plunger (9) is displaceable in relation to the cathode (5).

16. A device according to claim 15, characterized in that the plunger (9) has a hole formed therein through which the cathode (5) projects into the cathode space (7) when the plunger (9) is in its retracted position.

17. A device according to claim 8, characterized in that the casing (6) includes a through-penetrating hole that is spaced above the surface of liquid reagent and below the plunger when said plunger is in its retracted position, wherewith the level of liquid in the cathode space (7) adopts the same level as the surrounding liquid by virtue of pressure equalization; and in that the opening (8) has a narrower cross-sectional area than the internal cross-sectional area of said casing.

18. A device according to claim 2, characterized in that the cathode (5) is fixedly mounted to the plunger (9).

19. A device according to claim 2, characterized in that the plunger (9) is displaceable in relation to the cathode (5).

20. A device according to claim 19, characterized in that the plunger (9) has a hole formed therein through which the cathode (5) projects into the cathode space (7) when the plunger (9) is in its retracted position.

21. A device according to claim 2, characterized in that the casing (6) includes a through-penetrating hole that is spaced above the surface of liquid reagent and below the plunger when said plunger is in its retracted position, wherewith the level of liquid in the cathode space (7) adopts the same level as the surrounding liquid by virtue of pressure equalization; and in that the opening (8) has a narrower cross-sectional area than the internal cross-sectional area of said casing.

* * * * *

UNITED STATES PATENT AND TRADEMARK OFFICE
CERTIFICATE OF CORRECTION

PATENT NO. : 6,361,670 B1
DATED : March 26, 2002
INVENTOR(S) : Anders Cedergren

It is certified that error appears in the above-identified patent and that said Letters Patent is hereby corrected as shown below:

<u>Title page,</u>
Item [73], delete "AB Stockholms Patentyra" and substitute -- Teknikbrostiftelsen I Umeå -- in its place.

Signed and Sealed this

Twentieth Day of May, 2003

JAMES E. ROGAN
*Director of the United States Patent and Trademark Office*